United States Patent
Kappler (10) Patent No.: US 9,480,444 B2
(45) Date of Patent: Nov. 1, 2016

(54) X-RAY SYSTEM AND METHOD TO GENERATE IMAGE DATA

(71) Applicant: Steffen Kappler, Effeltrich (DE)

(72) Inventor: Steffen Kappler, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 188 days.

(21) Appl. No.: 14/026,236

(22) Filed: Sep. 13, 2013

(65) Prior Publication Data

US 2014/0072098 A1  Mar. 13, 2014

(30) Foreign Application Priority Data

Sep. 13, 2012  (DE) .................. 10 2012 216 269

(51) Int. Cl.
| | |
|---|---|
| A61B 6/03 | (2006.01) |
| A61B 6/00 | (2006.01) |
| G01N 23/04 | (2006.01) |
| G06T 7/00 | (2006.01) |

(52) U.S. Cl.
CPC ............ *A61B 6/4241* (2013.01); *A61B 6/032* (2013.01); *A61B 6/542* (2013.01); *G01N 23/046* (2013.01); *G06T 7/0012* (2013.01)

(58) Field of Classification Search
CPC ...... A61B 6/032; A61B 6/42; A61B 6/4241; A61B 6/52; A61B 6/5205; A61B 6/5211; A61B 6/54; A61B 6/542
USPC ...................... 378/6, 7, 19, 98.7, 98.8, 207; 250/370.09
See application file for complete search history.

(56) References Cited

U.S. PATENT DOCUMENTS

| | | | |
|---|---|---|---|
| 4,292,538 A | | 9/1981 | Carlson |
| 4,963,746 A | | 10/1990 | Morgan et al. |
| 5,469,429 A | * | 11/1995 | Yamazaki et al. .............. 378/19 |
| 5,495,514 A | * | 2/1996 | Horbaschek et al. ....... 378/98.2 |
| 5,509,044 A | * | 4/1996 | Horbaschek .................... 378/97 |
| 5,550,886 A | * | 8/1996 | Dobbs et al. ................... 378/19 |
| 5,566,220 A | * | 10/1996 | Saito et al. ................... 378/138 |
| 5,570,403 A | * | 10/1996 | Yamazaki et al. .............. 378/19 |
| 5,583,903 A | | 12/1996 | Saito et al. |
| 5,602,896 A | * | 2/1997 | Diepstraten ................. 378/98.7 |
| 5,635,714 A | | 6/1997 | Nablo et al. |
| 5,664,000 A | * | 9/1997 | Van Woezik et al. ....... 378/98.7 |
| 5,710,801 A | * | 1/1998 | Dillen et al. ................ 378/98.7 |
| 5,745,548 A | * | 4/1998 | Dobbs et al. ................ 378/207 |
| 5,867,553 A | * | 2/1999 | Gordon et al. ................... 378/4 |

(Continued)

FOREIGN PATENT DOCUMENTS

| | | |
|---|---|---|
| CN | 101435875 A | 5/2009 |
| CN | 101572130 A | 11/2009 |

(Continued)

*Primary Examiner* — Allen C. Ho
(74) *Attorney, Agent, or Firm* — Schiff Hardin LLP (57) ABSTRACT

An x-ray system, such as a computed tomography system, has an x-ray source, a projection detector arrangement associated with the x-ray source for the acquisition of projection data of an examination subject, and a monitor detector that measures current dose measurement data of the x-ray radiation. The monitor detector is designed and arranged to detect a portion of the x-ray radiation that does not travel through the examination subject. The monitor detector is formed as an energy-resolving detector. Furthermore, a method for the acquisition of projection data of an examination subject a method to generate image data make use of such an x-ray system.

18 Claims, 6 Drawing Sheets

(56) References Cited

U.S. PATENT DOCUMENTS

| | | | |
|---|---|---|---|
| 6,044,127 A * | 3/2000 | Van Bree et al. | 378/98.7 |
| 6,067,043 A * | 5/2000 | Faure et al. | 342/174 |
| 6,067,343 A * | 5/2000 | Brendler et al. | 378/98.7 |
| 6,084,940 A * | 7/2000 | Van Asten | 378/98.7 |
| 6,094,469 A * | 7/2000 | Dobbs et al. | 378/19 |
| 6,175,614 B1 * | 1/2001 | Jensen et al. | 378/98.7 |
| 6,198,801 B1 * | 3/2001 | Dillen | 378/98.7 |
| 6,208,710 B1 * | 3/2001 | Nagai | 378/108 |
| 6,333,965 B1 * | 12/2001 | Van Berkel | 378/98.7 |
| 6,516,098 B2 * | 2/2003 | Nonaka | 382/274 |
| 6,542,576 B2 * | 4/2003 | Mattson | 378/119 |
| 6,925,140 B2 * | 8/2005 | Bruder | 378/4 |
| 7,046,761 B2 * | 5/2006 | Ellenbogen et al. | 378/57 |
| 7,110,495 B2 * | 9/2006 | Tamegai | 378/97 |
| 7,116,752 B2 * | 10/2006 | Takahashi et al. | 378/62 |
| 7,145,150 B2 * | 12/2006 | Chugg | 250/370.01 |
| 7,266,179 B2 * | 9/2007 | Deuringer et al. | 378/137 |
| 7,284,905 B2 * | 10/2007 | Kuhn | 378/207 |
| 7,286,639 B2 * | 10/2007 | Shen et al. | 378/98.8 |
| 7,433,443 B1 * | 10/2008 | Tkaczyk et al. | 378/19 |
| 7,613,274 B2 * | 11/2009 | Tkaczyk et al. | 378/5 |
| 7,738,625 B2 * | 6/2010 | Nishide et al. | 378/19 |
| 7,894,576 B2 * | 2/2011 | Carmi | 378/98.9 |
| 8,077,826 B2 * | 12/2011 | Ruimi et al. | 378/7 |
| 8,111,803 B2 * | 2/2012 | Edic et al. | 378/5 |
| 8,243,874 B2 * | 8/2012 | Carmi | 378/5 |
| 8,442,184 B2 * | 5/2013 | Forthmann et al. | 378/5 |
| 8,611,489 B2 * | 12/2013 | Roessl | 378/5 |
| 8,714,818 B2 * | 5/2014 | Tesic et al. | 378/207 |
| 8,873,703 B2 * | 10/2014 | Ruimi et al. | 378/7 |
| 2008/0304726 A1 | 12/2008 | Fessler et al. | |
| 2009/0245467 A1 | 10/2009 | Wilson et al. | |

FOREIGN PATENT DOCUMENTS

| | | |
|---|---|---|
| DE | 10 2005 002 983 A1 | 8/2006 |
| DE | 102007027460 | 12/2008 |

* cited by examiner

X-RAY SYSTEM AND METHOD TO GENERATE IMAGE DATA

BACKGROUND OF THE INVENTION

1. Field of the Invention

The invention concerns an x-ray system, in particular a computed tomography system, with an x-ray source, a projection detector arrangement associated with the x-ray source for the acquisition of projection data of an examination subject, and a monitor detector to measure current dose measurement data of the x-ray radiation of the x-ray source, wherein the monitor detector is designed and arranged so that it detects a portion of the x-ray radiation that is not traveling through the examination subject. Moreover, the invention concerns a method to acquire projection data of an examination subject by means of such an x-ray system, as well as a method to generate image data.

2. Description of the Prior Art

Computed tomography is based on x-ray radiation that is emitted by an electron beam that strikes a target when a defined voltage is applied between the electron source and the target. The energy, or more precisely the energy spectrum, of the emitted x-ray radiation is dependent on the applied tube voltage, but the x-ray intensity depends on the applied amperage. The emission of x-ray radiation follows the buildup of a voltage and an amperage at the tube with a certain delay. The applied voltage or amperage and the bremsstrahlung that is thereupon emitted normally do not have a rise and fall response that are proportional to one another. Therefore, discrepancies can occur between the x-ray radiation energy that is determined on the basis of the applied voltage, and the actually emitted x-ray radiation energy, and between the x-ray intensity that is calculated on the basis of the applied current, and the actual intensity of the emitted x-rays. These discrepancies can be subject to additional variations, for example over the service life of the tube and due to aging processes.

Monitor detectors that measure an intensity of x-ray radiation emitted in proximity to the x-ray tube are known in computed tomography for the measurement of intensity fluctuations in the radiation emission. In coordination with the main detector of the CT scanner (with which the projection data are acquired), such monitors allow monitoring of the x-ray intensity and provide data for a correction of measurement data of the main detector. Conventional monitor detectors are designed as energy-integrating detectors that total the charges of the occurring x-ray photons in a defined measurement time period. However, this measurement method has limitations that occur (for example given a manner of operation known as dual energy computed tomography) when the x-ray tube is controlled with rapidly changing voltage and/or current strengths for the purposes of improved imaging, and therefore the tube generates x-ray radiation with different energy spectra. In particular in these methods with a fast voltage switching, due to the time delay of the voltage buildup at the x-ray source, particularly severe discrepancies can occur between the x-ray energy determined at the applied voltage and the actual current x-ray energy, and as a result adulterations can occur in the imaging or evaluations based on the image.

SUMMARY OF THE INVENTION

An object of the present invention is to improve a computed tomography system so as to achieve greater precision of the imaging of an examination subject.

The x-ray system according to the invention has at least one x-ray source, a projection detector arrangement associated with the x-ray source for the acquisition of projection data of an examination subject, and a monitor detector to measure current dose measurement data of the x-ray radiation emitted by the x-ray source in operation. The monitor detector is designed and arranged so as to detect a portion of the x-ray radiation that does not travel through the examination subject. The x-ray system differs from the prior art by the monitor detector being fashioned as an energy-resolving detector.

As used herein, the term "x-ray system" means a computed tomography system, but can also include a simple x-ray apparatus or an angiography apparatus, The x-ray source is an x-ray tube that preferably can be operated according to the dual energy or multi-energy principle. This is a control of the x-ray tube with at least two different voltage levels that results in an emission of x-ray radiation of different energies, or different wavelengths of x-ray bremsstrahlung. The term "energy" of the x-ray radiation (also designated as "x-ray energy" or "x-ray radiation energy") is understood in this context as an energy distribution or as an energy spectrum. An energy spectrum is represented by a value of the x-ray energy that typically represents a maximum or a mean value of the energy spectrum. The x-ray energy is typically indicated as a voltage value of the tube voltage set at the x-ray tube. Typical energy spectra that are applied in a computed tomography system with dual energy functionality are, for example, 80 kV and 140 kV. The x-ray tube can be designed such that a voltage applied to it, and possibly also the amperage, can be switched in short time intervals between at least two values, and thus the x-ray radiation can be switched between two corresponding energy spectra. This operation of the x-ray source of a computed tomography system is designated by the terms "fast kVp switching" or "fast kVp/mA switching".

The projection detector arrangement forms the main detector of the x-ray system and, in operation, can determine projection data of the examination subject arranged in a measurement field or measurement space. In a typical acquisition of x-ray projection data, the x-ray source emits radiation, with an x-ray fan beam or x-ray cone beam being shaped by means of a diaphragm. The fan beam or cone beam is projected in a primary radiation direction of the x-ray photons, through the examination subject, onto the projection detector arrangement. Depending on the thickness and material of the examination subject, the x-ray radiation is locally differently absorbed. A dose of the x-ray radiation propagating through the examination subject in the course of a measurement process is measured with spatial resolution by a number of detector elements of the projection detector arrangement. The projection data measured in such a manner thus include information about the local attenuation of the radiation in the subject. The projection data (called raw data) form the basis for generation of image data of the examination subject.

The monitor detector to acquire current dose measurement data is designed to measure an x-ray dose that an x-ray source emits while the projection detector arrangement conducts an acquisition of projection data of an examination subject. The monitor detector and the projection detector arrangement are therefore designed for simultaneous measurement of x-ray radiation. Both detectors are arranged facing the x-ray source in the x-ray system. In order to detect x-ray radiation that does not travel through the examination subject, the monitor detector is positioned such that the examination subject or another object cannot enter into the space between the x-ray source and the monitor detector (for example due to operator error). For example, the monitor detector can be arranged in proximity to the x-ray source. The x-ray source preferably emits x-ray radiation exhibiting a uniform radiation behavior, such that each defined unit of area within a dose of emitted x-ray radiation is identical with regard to the radiation behavior therein. This proves to be advantageous in the sense of comparability of the projection data and dose measurement data. Like the projection data, the dose measurement data also form unprocessed raw data.

X-ray radiation that does not travel through the examination subject positioned in a measurement space of the x-ray system can be, for example, unattenuated x-ray radiation. Unattenuated radiation is used to calibrate the x-ray system, for instance in a scan known as an air scan (air acquisition), i.e. an x-ray projection through environmental air.

An energy-resolving monitor detector can differentiate x-ray radiation with at least two different energies. This means that it can detect dose values of incident x-ray photons separately for at least two different energy ranges. Information about the energy of an x-ray photon can allow a conclusion to be made of the voltage that was actually applied to the x-ray source at the point in time of the emission of the x-ray photon. This actual voltage can differ from a nominal voltage, for example due to the rise and/or fall behavior of the x-ray source. A calculated, actual voltage value can be associated with the same point in time as the dose measurement data of acquired projection data. This is particularly advantageous given operation of the x-ray source with "fast kVp switching", since the voltage that is actually applied at the x-ray source at a defined point in time cannot be measured at the x-ray source itself. At least a lower voltage and a voltage that is high relative to this can thus be differentiated by means of the energy-resolving monitor detector. Moreover, actual voltage values deviating from nominal voltage values can advantageously be determined. The measurement data provided by the energy-resolving monitor detector can advantageously be used in the subsequent data processing and image reconstruction chain, for example in the fine tuning of correction steps. The invention goes beyond the prior art because the energy-resolving, measuring monitor detector enables a more precise measurement of the emitted x-ray radiation and can thereby produce an improvement of the imaging.

A method according to the invention for the acquisition of projection data of an examination subject makes use of an x-ray system that has at least one x-ray source as described above. The x-ray system can be a computed tomography system, but can also be designed as a simple x-ray apparatus or angiography apparatus, for example. The method includes at least the steps of acquisition of projection data of the examination subject by means of a projection detector arrangement associated with the x-ray source, and acquisition, with a monitor detector, of current dose measurement data of a portion of the x-ray radiation that does not travel through the examination subject. A significant feature of the method according to the invention is that the measurement of the current dose measurement data is implemented in an energy-resolving manner. The cited steps of a separate data acquisition preferably take place simultaneously, for example by synchronization of the measurement processes by the projection detector arrangement and the monitor detector. X-ray radiation that does not travel through the examination subject positioned in a measurement space of the x-ray system can be, for example, unattenuated x-ray radiation.

The invention moreover encompasses a method to generate image data that includes at least the method steps described in the following. An initial step is preparation of projection data that were acquired in a preceding step by means of a projection detector arrangement of the x-ray system. The x-ray system can be a computed tomography system. This is followed by preparation of current dose measurement data that were detected by a monitor detector from a portion of the x-ray radiation that does not travel through the examination subject. Moreover, the method further includes generation of the image data on the basis of the projection data using the dose measurement data of the monitor detector.

The preparation of projection data and dose measurement data after their acquisition via separate measurement devices can be implemented by a data transfer from the measurement devices to a control device of the x-ray system. The provision can similarly take place by data transfer into an intermediate storage, from which the data are the available for further data processing and are retrievable for the implementation of arbitrary method steps. Image data can be obtained from projection data in the application of known image generation methods. The image data can include an image of the examination subject—for example in the form of slice images, 3D images or even 4D image data (with a time component—and be presented at a display (a screen, for example). The use of current dose measurement data (that are acquired simultaneously with projection data) in the generation of the image data can produce a greater precision and/or a correction of the image data, as described. The use of the current dose measurement data can take place such that correction factors are determined from these, which correction factors are incorporated into a generation of image data from projection data. Information about the energy of the x-ray photons and/or about an actual voltage of the x-ray source can additionally be obtained from the dose measurement data, which information can be integrated into the file headers of image data (which were generated from projection data), for example. In this case, the image data indirectly include the information obtained from dose measurement data. The generation of image data can take place in an image generation unit that can in turn be a component of a control device. Some parts of the control device—for example a reconstruction device to reconstruct the image data from the projection data using the dose measurement data—can also be realized as software at suitable computers, i.e. do not need to be realized purely in hardware.

A realization largely in software has the advantage that existing x-ray systems can be retrofitted simply by means of a software update in order to operate in the manner according to the invention. Therefore, the invention also encompass a non-transitory, computer-readable data storage medium encoded with programming instructions that, when the storage medium is loaded into a memory of a programmable control device and/or an image generation unit of an x-ray system (in particular computed tomography system), cause all steps of the method according to the invention to be executed by the control device and/or image generation unit.

In a preferred embodiment, the x-ray system according to the invention has a control device that is designed so that, in operation, it controls the projection detector arrangement and the monitor detector for synchronized (temporally parallel) acquisition of projection data and dose measurement data. The term "operation" of the x-ray system designates a functional state in which all elements of the device—and therefore also the control device—are activated and implement defined workflows that lead to the acquisition of desired data sets. Control of the projection detector arrangement and of the monitor detector by the control device can take place by means of clock signals or via triggers, for which a special trigger unit can be used, or a trigger unit that is used to control the projection detector arrangement anyway can be used as well for the monitor detector. The control device also preferably controls the x-ray source such that the emission of x-ray radiation is synchronized with the measurements (i.e. the raw data acquisition) by the projection detector arrangement and the monitor detector. The synchronized (and advantageously simultaneous) acquisition of projection data and dose measurement data offers the advantage that the dose measurement data can be associated with exactly those projection data that were acquired at an identical point in time after an emission of x-ray radiation. In particular, given a rapid switching between voltages at the x-ray tube—for example given "fast kVp switching"—this association forms the basis for a later correction and/or more precise rendering in the further processing of the acquired projection data, or image data based on these, in subsequent data processing processes.

The described control device of the x-ray system is designed so that projection data acquired by the projection detector arrangement and/or image data reconstructed on the basis of the projection data are linked with dose measurement data detected in a time-correlated manner with these by the monitor detector, or energy data based on the dose measurement data. As explained, projection data and dose measurement data are detected separately from one another by separate measurement devices. These raw data can both be further processed separately and be combined or linked in various intermediate stages of the processing. Projection data can accordingly be processed into image data with or without a use of dose measurement data. Dose measurement data can be linked with projection data or be processed separately into energy data. As used herein, "energy data" are data which include information regarding the energy of the x-ray photons that struck the monitor detector at the point in time of measurement. The energy data can be further processed into data that include information about an actual voltage that was applied to the x-ray source at the point in time of the emission of the x-ray radiation. The process of linking can lead into an immediate processing of the linked data, or into a linked storage in a cache.

The projection data or image data can be linked in any manner with dose measurement data or energy data, for example be stored in common or be linked via pointers. The linking of the data can, for example, take place in the combination unit as a component of the control device. The process of linking has proven to be advantageous in that it forms a requirement for a correct association of simultaneously acquired projection data and dose measurement data, and therefore for an improved imaging of an examination subject.

According to a preferred embodiment, the x-ray system has an image generation unit which is designed so that it generates image data on the basis of the projection data, wherein temporally correlated, acquired dose measurement data or energy data based on these are used in addition to the projection data. For example, the image generation unit can execute a reconstruction of image data from projection data, wherein the dose measurement data or, respectively, energy data enter directly into the reconstruction. For this purpose, the reconstruction unit must be designed accordingly in order to be able to process the dose measurement data or, respectively, energy data. Alternatively or additionally, a generation of correct mixed images formed by already-reconstructed image data can also take place after the reconstructed images have been associated with corresponding (correct) energy data. The reconstruction unit also can be designed to integrate associated energy data into a file header of the image data. One component of the image generation unit can be a reconstruction unit; the image generation unit can itself be a component of the control device. The image generation unit offers the advantage of a further processing of measurement data into image data that can simply be evaluated for the user, for example via a screen.

The monitor detector of the x-ray system is advantageously arranged in the region of a diaphragm facing towards the x-ray source. In operation, the x-ray source radiates the x-ray radiation to all sides. The diaphragm is arranged between the x-ray source and the projection detector arrangement, and particularly preferably in immediate proximity to the x-ray source. The diaphragm can have an opening whose edge defines the lateral extent of the x-ray fan or cone beam which goes from the x-ray source through the diaphragm aperture into the measurement field and travels in the direction of the projection detector arrangement. In contrast to this, a closed region can block the transmission of x-ray radiation. The monitor detector can be positioned before or after the diaphragm in a primary photon radiation direction pointing from the x-ray source in the direction of the projection detector arrangement, or can be integrated into the diaphragm arrangement. The detection area of the monitor detector is accordingly advantageously smaller, and particularly preferably smaller by a multiple, than the detection area of the projection detector arrangement. The term "primary photon radiation direction" in this context designates a direct radiation direction from the x-ray source to the projection detector arrangement. The monitor detector is advantageously directly charged with x-ray radiation in every arrangement. The incident x-ray radiation can be "unattenuated", which means that any attenuation is caused only by environmental air. In one position of the monitor detector that lies after the diaphragm in the primary photon radiation direction, the diaphragm therefore advantageously has an aperture that permits a direct charging of the monitor detector with x-ray radiation. The arrangement of the monitor detector according to the invention has proven to be advantageous since the danger of an indeliberate attenuation of the x-ray radiation incident at the monitor detector in immediate proximity to the x-ray source is reduced.

According to an alternative preferred embodiment of the x-ray system, the monitor detector is positioned at the projection detector arrangement or integrated into the projection detector arrangement. For example, the monitor detector can be arranged next to or in a boundary region of the detection area of the projection detector arrangement, such that the x-ray fan beam that is incident in the measurement field, through the diaphragm aperture, reaches the monitor detector at the same intensity as the main detector in the form of the projection detector arrangement. This embodiment offers the advantage that a separate arrangement of a further detector element is not necessary. The complexity of the x-ray system can thereby be reduced. In principle, the x-ray system can comprise a plurality of similarly or differently designed monitor detectors.

The monitor detector preferably has at least two energy-integrating detector elements, upstream of which are respectively different radiation filters. Energy-integrating x-ray detectors can be designed so as to determine a dose or a sum of all incident x-ray photons during a defined measurement time period, independent of their respective energy insofar as the energy and the dose lie in the measurement range of the detector. The detection of the x-ray dose takes place indirectly via a measurement of the charges of the x-ray photons converted into electrons, which charges are released in the detector. Spectral filters for filtering x-ray radiation can block defined portions (i.e. wavelength ranges) of radiation spectra.

Radiation filters are preferably located upstream of the energy-integrating detector elements in the primary photon radiation direction, which radiation filters block at least two different radiation spectra. A first radiation filter absorbs low-energy (soft, i.e. relatively long-wave) x-ray radiation; a second radiation filter absorbs high-energy (hard, i.e. relatively short-wave) x-ray radiation relative to this. The different embodiment of the radiation filters is designed for a high energy separation. For example, suitable radiation filters comprise the construction materials aluminum, tin or platinum and have a defined thickness depending on their absorption strength.

The advantage of such an embodiment is that energy-integrating x-ray detectors can detect high radiation intensity and are cost-effective. The use of different radiation filters according to the invention enables an energy-resolving measurement of x-ray radiation. A low-energy x-ray radiation is filtered by a filter that is designed to absorb low-energy x-ray radiation, such that only a low electron flow can be measured at a detector element arranged after this in the primary radiation direction of the x-ray photons. A high electron flow can thereby be simultaneously measured at a detector element, upstream of which is arranged a radiation filter which is designed to absorb high-energy x-ray radiation. Given a synchronized measurement of the projection detector arrangement and the monitor detector, the correlation of the electron flow rates at both detector elements enables a simple association of a data set acquired via the projection detector arrangement with an actual voltage applied to the x-ray tube at this point in time or in the time period of the measurement.

As an alternative to the aforementioned energy-integrating detector elements, the monitor detector of the x-ray system can be formed by at least one photon-counting detector element that has at least two different energy thresholds. An energy threshold determines the registration of an x-ray photon striking the detector element. The detector element is designed to count x-ray photons with an energy between the first energy threshold and the second energy threshold and x-ray photons with a higher energy than the second energy threshold separately from one another, with the second energy threshold being higher than the first energy threshold. The at least two energy thresholds are advantageously selected to be situated far from one another in the sense of a high energy separation and, for example, lie at energy levels that correspond to a voltage of 80 kV and 120 kV applied to the x-ray tube. The counting of the x-ray photons takes place indirectly in that the detector element converts x-ray photons into electrons whose released charges are measured. The monitor detector can have a number of photon-counting detector elements. The preferred embodiment of the monitor detector offers the advantage of a precise measurement of the x-ray photons emitted by the x-ray source and striking the detector surface of the monitor detector in the primary radiation direction. The different energy threshold values of the detector element of the monitor detector enable an energy-resolving measurement of the incident x-ray radiation. The respective effective or, respectively, actual voltage that is applied to the x-ray tube at a defined measurement point in time can thereby be calculated very precisely.

As an alternative to the two described embodiments of the monitor detector, it can be formed as a combination of both detector types so that it has at least two detector elements that are arranged one after another in a primary photon radiation direction, with each detector element being designed to be energy-integrating or photon-counting. The primary photon radiation direction is situated at a right angle or an angle to a detector surface of a monitor detector. In principle, the monitor detector can have a number of detector layers and/or multilayer detector elements. It can have a detector element with at least two layers, which is designed so that the at least two detector layers measure different energy spectra of incident x-ray radiation. The detector element can thus have a layer of an energy-integrating detector and a layer of a photon-counting detector that can be arbitrarily arranged in the primary proton radiation direction. In principle, both layers can be designed for the detection of low-energy or high-energy x-ray radiation. The combination of both detector types permits a measurement of incident x-ray photons at high energy separation to take place. This embodiment of the monitor detector merges the described advantages of the energy-integrating and photon-counting detector types. Moreover, other combinations of the described detector types are possible.

The method according to the invention that is described above for the acquisition of projection data of an examination subject is preferably designed such that the x-ray source is controlled during a measurement process or between two measurement processes so that projection data with different x-ray energies are acquired in different time segments, and energy data for the different time segments are respectively determined on the basis of the dose measurement data of the monitor detector. As mentioned, the x-ray source is designed as an x-ray tube that is switched between two voltage strengths and/or amperages so that it alternately emits low-energy and high-energy x-ray radiation. The switching particularly preferably takes place at high frequency. In this context, a sum of measurements of an examination subject extending in a spatial volume is understood as a measurement process, which measurements are regularly implemented in order to generate slice images and/or volume images of said examination subject. Given the preferred alternating emission of low-energy and high-energy x-ray radiation by the x-ray source, the time segments in which projection data and dose measurement data are acquired given a low-energy radiation and in which projection data and dose measurement data are acquired given a radiation that is relatively high-energy in comparison to this are determined separately and are totaled up or, respectively, computed separately. The totaled time segments can then represent an "exposure time" per volume segment (or for a single slice image) of the examination subject for an x-ray energy. Since the dose measurement data were acquired with a portion of x-ray radiation passing through the examination subject, they can be effective as a reference for the evaluation of the simultaneously acquired projection data. A proximity of the dose measurement data into energy data with application of defined calculation methods can thus yield information about which x-ray energy was measured in which time segment. As a result, this method can achieve the same positive effect as if the examination subject were scanned with a low-energy x-ray radiation in a first concluded measurement process and with a high-energy x-ray radiation in a second concluded measurement process, and the measurement data are subsequently offset against one another. However, the advantage of a procedure that embodies the method according to the invention is a marked reduction of negative influences on the quality of the images of the examination subject that can result from a movement of the examination subject, in particular when an in vivo scan of a living organism (a human or animal, for example) is implemented.

According to a preferred embodiment, the method for generation of image data explained above includes the step of using the dose measurement data of the monitor detector directly in a reconstruction of image data on the basis of the projection data. A "reconstruction" is a calculation of slice image data and/or volume image data of the examination subject from the projection image data. The reconstructed image data can advantageously include a corrected imaging of the examination subject that was enabled via an energy-resolving acquisition of dose measurement data. For example, the corrected imaging can yield the advantage of an ability to better differentiate structures within the examination subject. The known method steps can be implemented in the control device of the x-ray system, and preferably in the reconstruction unit, and/or in a data processing unit (a computer system, for example) connected to the control device. In different intermediate steps of the method, data sets can be cached in a memory unit and then be re-supplied to the processing chain via a data processing unit.

The method to generate image data moreover preferably includes method steps according to which the dose measurement data of the monitor detector are used to generate energy data, and the energy data are used in a generation of mixed image data from image data. The image data were thereby previously reconstructed from projection data of the projection detector arrangement that were acquired at different x-ray energies. In comparison to the previously described embodiment of the method, a merging of further processed data that were generated from separately acquired projection data and dose measurement data is implemented, here after the step of reconstructing image data. The mixed image data can be corrected image data, wherein energy data with regard to the current values for x-ray energies were used for the correction process. The method steps can be implemented in the control device of the x-ray system and/or in a data processing unit connected to the control device. In different intermediate steps of the method, data sets can be cached in a memory unit and then be re-supplied to the processing chain.

DESCRIPTION OF THE PREFERRED EMBODIMENTS

Figure 1:
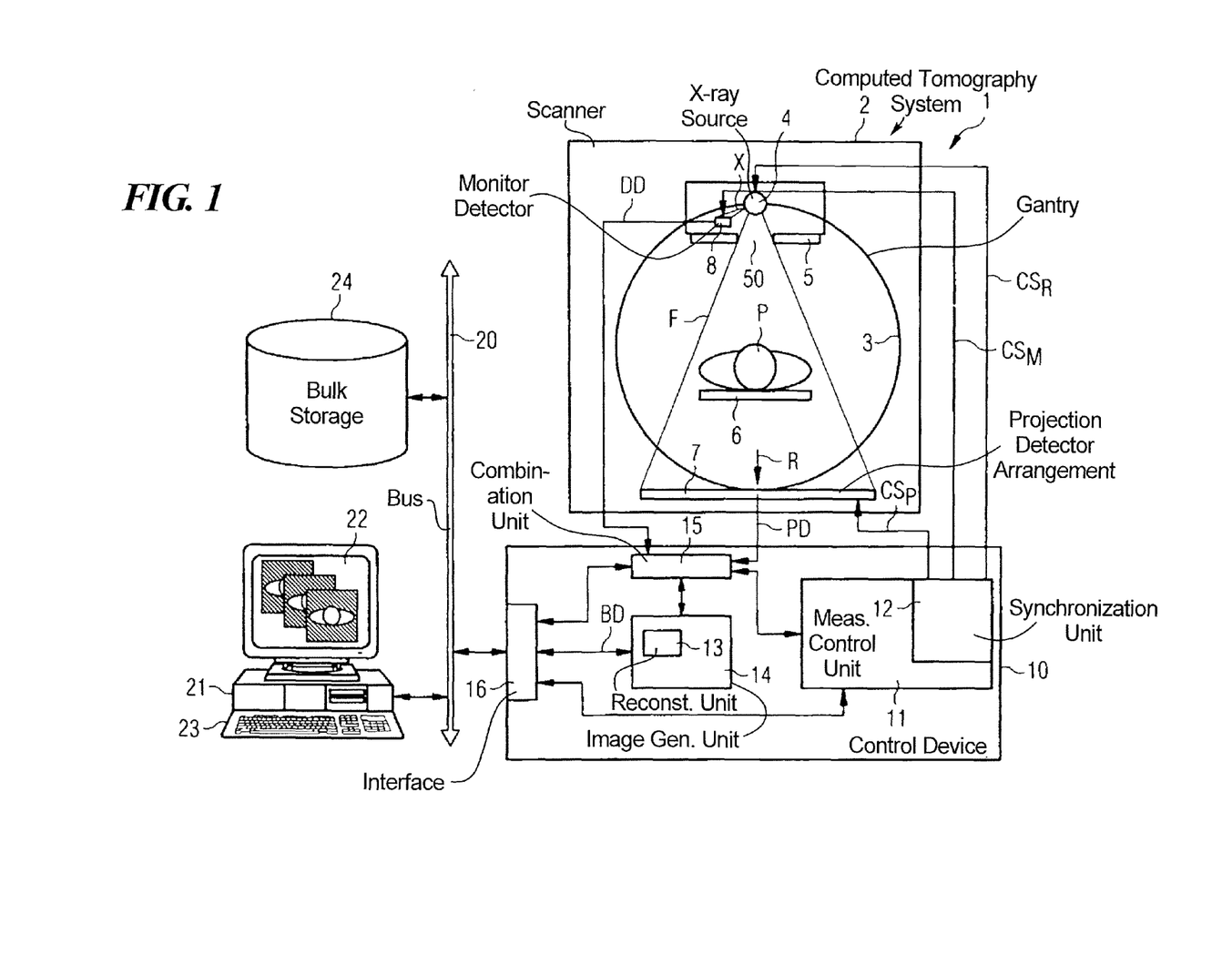
FIG. 1 schematically illustrates a computed tomography system according to a first embodiment of the invention.

FIG. 1 shows a computed tomography system 1 with a scanner 2 to acquire projection data PD of an examination subject P using x-ray radiation X. In a measurement process, the examination subject P is positioned on a table 6 that is located in a measurement space defined by a gantry 3 of the computed tomography system 1. On opposite sides of the measurement space of the gantry 3, an x-ray source 4 and a projection detector arrangement 7 to measure x-ray radiation X are arranged facing one another on the gantry 3, which x-ray source 4 and projection detector arrangement 7 move concentrically around the measurement space in operation of the computer tomography system 1 without moving relative to one another. In operation, the x-ray source 4 radiates x-ray radiation X that is partially absorbed by a diaphragm 5 on a side of the x-ray source 4 that faces the projection detector arrangement 7. The diaphragm 5 has a first diaphragm aperture 50 through which x-ray radiation X penetrates into the measurement space 3 in a primary photon radiation direction R. The x-ray radiation X is designated as an x-ray fan beam F after its exit from the first diaphragm aperture 50 of the diaphragm 5. Given a corresponding shape of the diaphragm 5, the x-ray radiation X can also alternatively form an x-ray cone beam after exiting the first diaphragm aperture 50. The first diaphragm aperture 50 is dimensioned such that the x-ray fan beam F charges at least one entire detection surface of the projection detector arrangement 7 upon striking the projection detector arrangement 7. At a slight distance from the x-ray source 4, a monitor detector 8 for measuring x-ray radiation X is arranged in a region between the x-ray source 4 and the diaphragm 5. The monitor detector 8 faces toward the x-ray source 4 and has a smaller detection area than the projection detector arrangement 7, and is not reached by (struck by) the x-ray fan beam F in the operating state. As a section of the entire x-ray radiation X, the x-ray fan beam F has, in each unit of solid radiation angle, the same intensity and x-ray energy as the x-ray radiation X per time unit and at a defined point in time.

Figure 7:
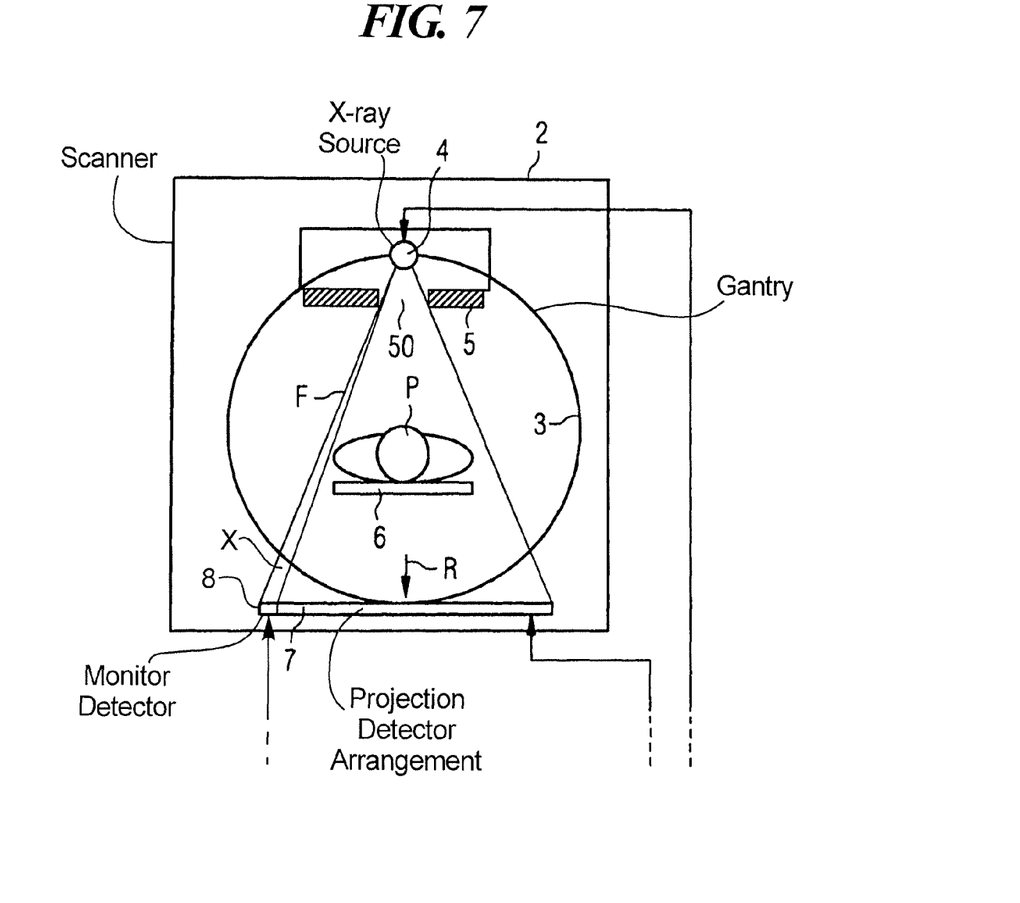
FIG. 7 is a sectional view of a computed tomography system according to a third embodiment of the invention.
Figure 8:
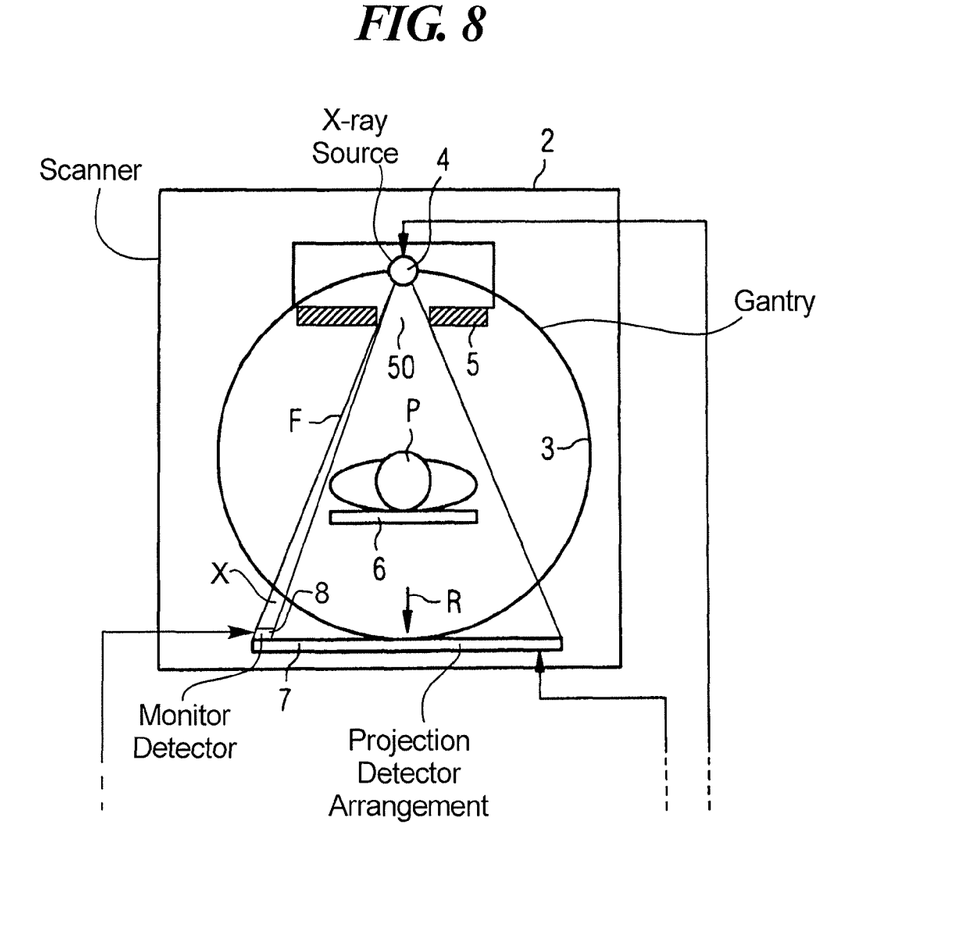
FIG. 8 is a sectional view of a computed tomography system according to a fourth embodiment of the invention.

FIG. 7 schematically illustrates a further embodiment wherein the monitor detector 8 is integrated in the projection detector arrangement 7. FIG. 8 schematically illustrates a further embodiment wherein the monitor detector 8 is situated at the projection detector arrangement.

In operation of the computed tomography system 1, the x-ray source 4 emits x-ray radiation X with at least two different energy spectra (dual energy CT/multi-energy CT), wherein the energy spectra alternate or, respectively, are switched at high frequency (fast kVp/mA switching). The monitor detector 8 possesses at least two detector elements with different sensitivity to x-ray energies. It can thereby implement an energy-resolving measurement of the x-ray photons emitted by the x-ray source 4. The projection detector arrangement 7 possesses a plurality of detector elements to generate projection data PD of the examination subject P arranged in the measurement space of the gantry 3. In a measurement, the monitor detector 8 generates dose measurement data DD about the dose of x-ray radiation X that strikes its detection area during a defined measurement time period. The x-ray radiation X is thereby only radiated through environment air. The projection detector arrangement 7 generates projection data PD about the dose of x-ray radiation X that strikes at various detector elements of the projection detector arrangement 7 during the measurement time period after they have been projected by x-ray source 4 through an examination subject P.

Moreover, the computed tomography system 1 has a control device 10 to process data and emit control signals to the scanner 2. The control device 10 is connected with the projection detector arrangement 7 and the monitor detector 8. It is also connected via an interface 16 with a bus 20 for data transport. A terminal 21 for data processing, with a screen 22 and an operating unit 23, is connected to the bus 20 at one end; a bulk storage 24 is connected at the other end. The bus 20 can also be connected, for example, to a radiological information system (RIS). The connections between all elements, devices and units of the computer tomography system 1 that are shown in FIG. 1 are fashioned as electronic two-way connections for the dispatch and reception of signals.

The control device 10 has a measurement control unit 11 with a synchronization unit 12. The control device 10 is designed in order to automatically control the entire CT system 1 to implement defined measurements or, respectively, to acquire defined image data on the basis of predetermined measurement protocols that can be selected and modified by the operator, wherein the reconstruction of the image data can also hereby be predetermined. However, the principle of the mode of measurement is known to those skilled in the art and therefore need not be explained further herein. The synchronization unit 12 of the measurement control unit 11 thereby controls the x-ray source 4, the projection detector arrangement 7 and the monitor detector 8 such that the emission of x-ray radiation X and the simultaneous measurement of the emitted x-ray radiation X by the projection detector arrangement 7 and the monitor detector 8 take place within a defined time interval. This control takes place by emission of clock signals $CS_R$, $CS_M$, $CS_P$ from the synchronization unit 12 to the x-ray source 4 ($CS_R$), to the monitor detector 8 ($CS_M$) and to the projection detector arrangement 7 ($CS_P$).

Moreover, here the control device 10 comprises a combination unit 15 for linking dose measurement data DD and projection data PD which were previously acquired in a common measurement time period or, respectively, at an identical measurement point in time. The control device 10 also has an image generation unit 14 to generate image data BD that comprises a reconstruction unit 13 to reconstruct image data BD from projection data PD. The image data BD include an image of the examination subject P in the form of slice images and can be presented at a screen 22. Moreover, the control device 10 has an interface 16 which transmits data from the control device 10 to the bus 20.

The dose measurement data DD and projection data PD acquired in a common measurement time period can be linked in the combination unit 15. They can alternatively be directly conducted to the reconstruction unit 13, which can generate image data BD from the dose measurement data DD and the projection data PD. According to a further alternative, image data BD can be generated from projection data PD without use of dose measurement data DD or energy data ED based thereon. In a further step of the data processing, mixed image data MD can be generated under incorporation of energy data ED from image data BD (reconstructed conventionally or using the dose measurement data DD or, respectively, energy data ED).

Figure 2:
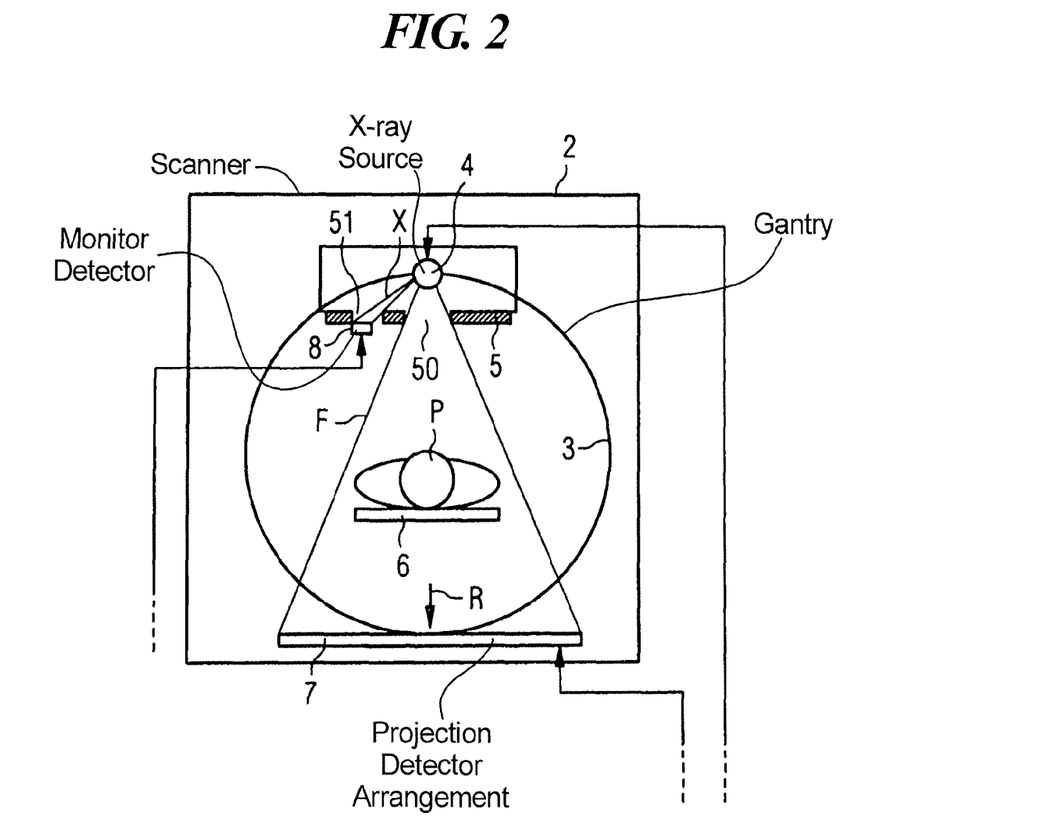
FIG. 2 is a sectional view of a computed tomography system according to a second embodiment of the invention.

In comparison to FIG. 1, the position of the monitor detector 8 in the scanner 2 is varied in FIG. 2. The monitor detector 8 here is arranged in or after the second diaphragm aperture 51 of the diaphragm 5 in the primary photon radiation direction R, the area of which second diaphragm aperture 51 is not greater than the detector area of the monitor detector 8. The x-ray fan beam F passing through the first diaphragm aperture 50 of the diaphragm 5 is thus not negatively affected by the second diaphragm aperture 51 of the diaphragm 5. In operation of the computed tomography system 1, the monitor detector 8 is exposed by the x-ray radiation X that is emitted by the x-ray source 4.

Figure 3:
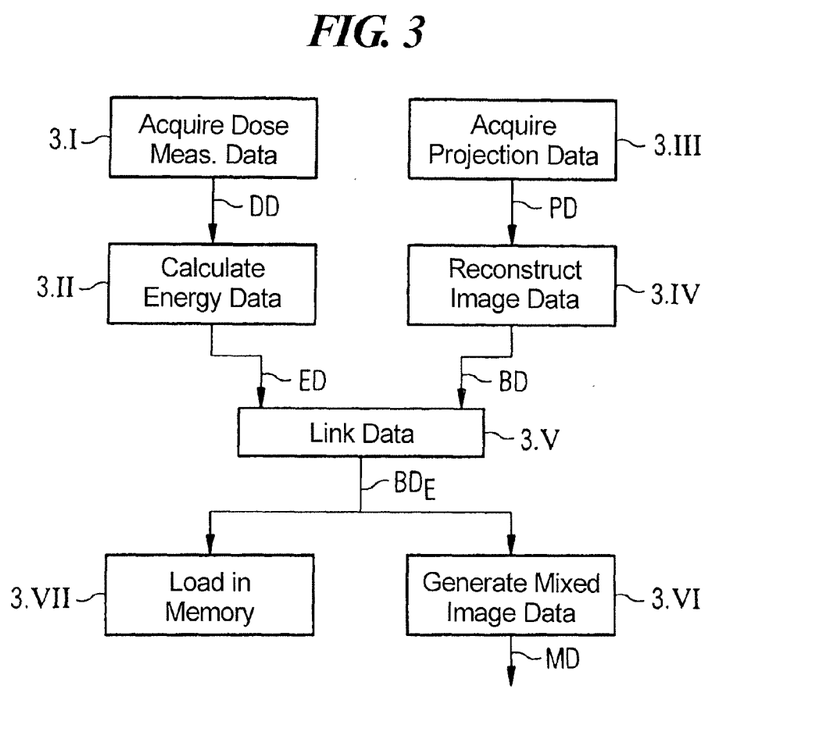
FIG. 3 is a flow chart for processing data via a control device of a computed tomography system according to a first embodiment of the invention.

FIG. 3 shows a process of measurement data acquisition and processing according to a first embodiment. In a first measurement (Step 3.III), the acquisition of the projection data PD takes place; in a second, temporally parallel measurement (Step 3.I), the acquisition of the dose measurement data DD is implemented separately. The respective data acquisitions in Steps 3.I and 3.III are conducted separately without the data DD and PD being mixed with one another. From the dose measurement data DD, energy data ED are initially calculated (Step 3.II) that include information about x-ray energies in defined time segments. Image data BD are reconstructed from the projection data PD (Step 3.IV). Energy data ED and image data BD are thereupon linked (Step 3.V) into image/energy data $BD_E$ that include information about at what x-ray energy a respective set of image data BD was generated. This image/energy data $BD_E$ can either be loaded into a memory (Step 3.VII) or be used to generate mixed image data MD in a further processing step (Step 3.VI). The mixed image data MD represent corrected image data BD, wherein energy data ED with regard to the actual values for x-ray energies were used for the correction process. Cached data can respectively form the basis of further data processing steps.

Figure 4:
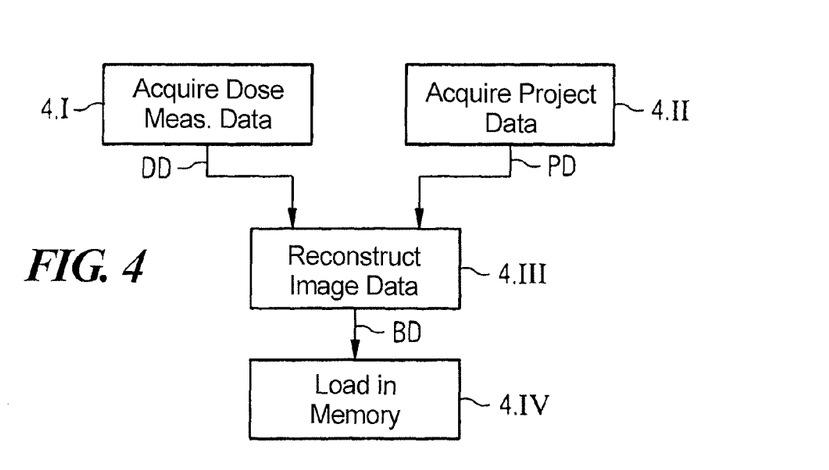
FIG. 4 is a flow chart for processing data via a control device of a computed tomography system according to a second embodiment of the invention.

The process of measurement data acquisition (Steps 4.I; 4.II) and processing differs from the workflow illustrated in FIG. 3 by virtue of the reconstruction of image data BD (Step 4.III) from projection data PD taking place directly using dose measurement data DD. A calculation of energy data ED from dose measurement data DD can therefore be omitted but is not precluded. After the reconstruction, the image data BD are loaded into a memory (Step 4.IV). A generation of mixed image data MD is also possible later in this embodiment, analogous to FIG. 3.

Figure 5:
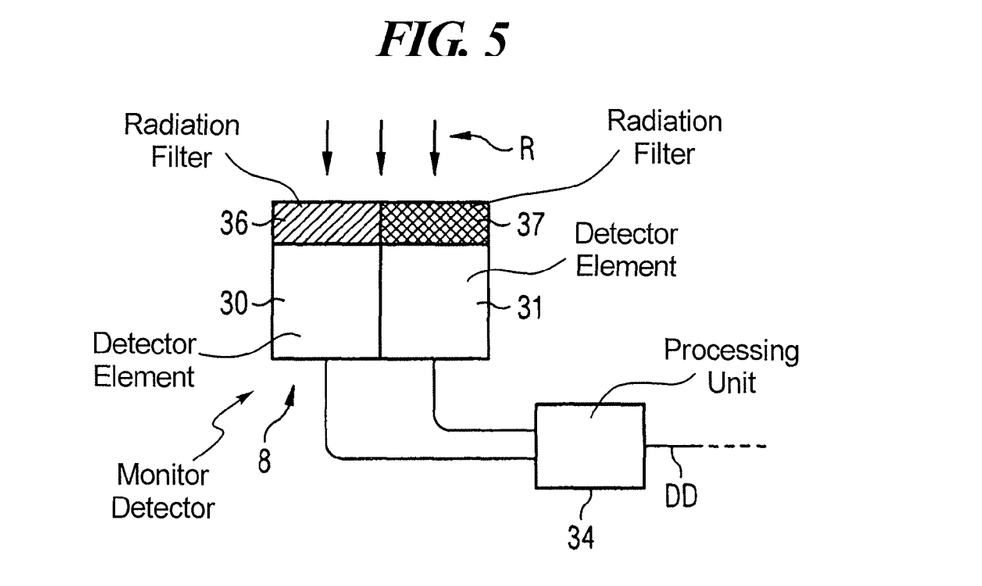
FIG. 5 schematically shows a monitor detector according to a first embodiment of the invention.

FIG. 5 shows a monitor detector 8 with two detector elements 30, 31 that are arranged next to one another in a primary photon radiation direction R, such that a first portion of the x-ray photons strikes the detector element 30 and is measured there and a second portion of the x-ray photons is measured by the detector element 31. The detector elements 30, 31 are designed according to the energy-integrating principle. They differ via radiation filters 36, 37 that are designed to have different strengths, of which respectively one radiation filter is upstream of a detector element in the primary photon radiation direction R. This embodiment enables an energy-resolving measurement of the x-ray radiation X via the monitor detector 8. Both detector elements 30, 31 are connected to a processing unit 34; the incoming signals of the detector elements 30, 31 are processed into dose measurement data DD.

Figure 6:
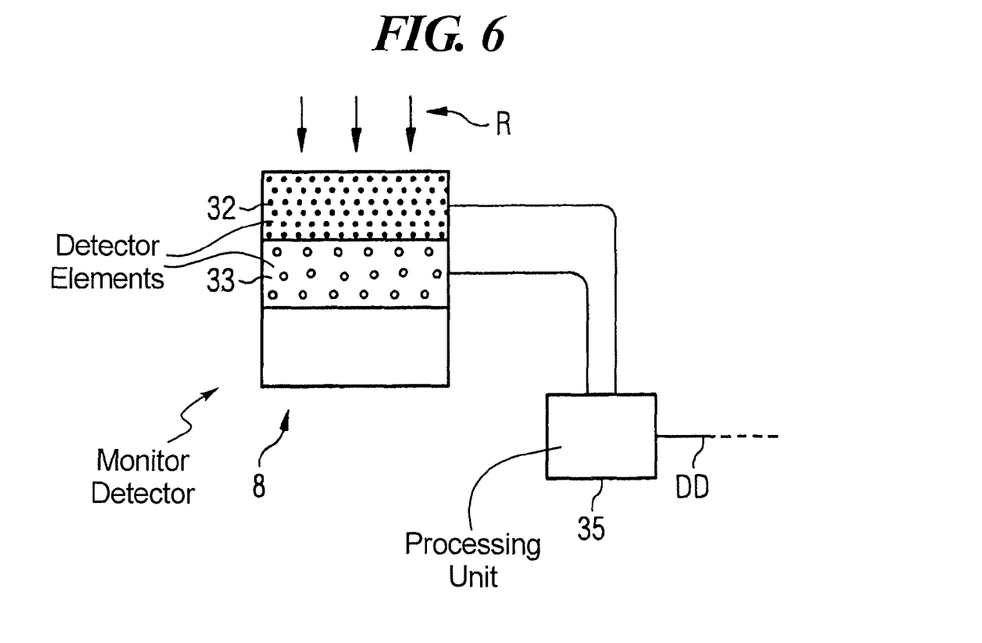
FIG. 6 schematically shows a monitor detector according to a second embodiment of the invention.

FIG. 6 shows a monitor detector 8 in multilayer formation with two detector elements 32, 33 that are arranged one after another in a primary photon radiation direction R, such that a first portion of the x-ray photons strikes the detector element 32 and is measured there and a second portion of the x-ray photons runs through the detector element 32 and is measured at the detector element 33. Both detector elements 32, 33 are connected to a processing unit 35 that processes incoming signals of the detector elements 32, 33 into dose measurement data DD. While the detector element 32 is designed according to the photon-counting principle, the detector element 33 operates according to the energy-integrating principle. An energy-resolving measurement of the x-ray radiation X by the monitor detector 8 is thereby enabled.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray system, comprising:
    an x-ray source that emits x-ray radiation;
    a radiation detector located in a path of said x-ray radiation that detects at least x-ray radiation attenuated by an examination subject irradiated by said x-ray radiation, and that generates two-dimensional radiation detector data corresponding to said x-ray radiation attenuated by the examination subject;
    a monitor detector irradiated by said x-ray radiation emitted by said x-ray source that does not travel through said examination subject, said monitor detector being configured as an energy-resolving detector to generate energy-resolved current dose measurement data representing a current dose of said x-ray radiation; and
    said monitor detector comprising at least two detector elements located in succession in a direction of propagation of said x-ray radiation, each of said at least two detector elements being a detector element selected from the group consisting of an energy-integrating detector element and a photon-counting detector element.

2. An x-ray system as claimed in claim 1, wherein said x-ray source and said radiation detector are configured to operate as a computed tomography system, with said two-dimensional radiation detector data generated by said radiation detector representing projection data obtained by irradiation of an examination subject from respectively different directions.

3. An x-ray system as claimed in claim 1, comprising a control unit configured to control said radiation detector and said monitor detector to synchronously acquire said two-dimensional radiation detector data from said radiation detector and said energy-resolved current dose measurement data from said monitor detector.

4. An x-ray system as claimed in claim 3, wherein said control unit is configured to operate said radiation detector and said monitor detector to acquire said two-dimensional radiation detector data from said radiation detector and said energy-resolved current dose measurement data from said monitor detector temporally in parallel.

5. An x-ray system as claimed in claim 3, wherein said control unit is configured to operate said radiation detector and said monitor detector to acquire said two-dimensional radiation detector data from said radiation detector and said energy-resolved current dose measurement data from said monitor detector linked together with a temporal correlation.

6. An x-ray system as claimed in claim 5, comprising an image generation unit supplied with said two-dimensional radiation detector data from said radiation detector and said energy-resolved current dose measurement data from said monitor detector, and configured to generate image data from said two-dimensional radiation detector data acquired by said radiation detector also using said temporally correlated energy-resolved current dose measurement data from said monitor detector.

7. An x-ray system as claimed in claim 1, wherein said x-ray source comprises a diaphragm that limits a size of a cross-section of said x-ray radiation, and wherein said monitor detector is arranged at said diaphragm facing toward said x-ray source.

8. An x-ray system as claimed in claim 1, wherein said monitor detector is located at said radiation detector.

9. An x-ray system as claimed in claim 1, wherein said monitor detector is integrated into said radiation detector.

10. An x-ray system as claimed in claim 1, wherein said monitor detector comprises at least two energy-integrating detector elements and respectively different radiation filters respectively located upstream, with respect to a direction of propagation of said x-ray radiation, of said at least two energy-integrating detector elements.

11. An x-ray system as claimed in claim 1, wherein said monitor detector comprises at least one photon-counting detector element comprising at least two different energy thresholds.

12. A method to operate an x-ray imaging system, comprising:
    irradiating an examination subject with x-ray radiation emitted from an x-ray source;
    detecting, with a radiation detector, said x-ray radiation attenuated by the examination subject and generating, from said radiation detector, two-dimensional radiation detector data representing the x-ray radiation attenuated by the examination subject;
    providing an energy-resolving monitor detector comprising at least two detector elements located in succession in a direction of propagation of said x-ray radiation, each of said at least two detector elements being a detector element selected from the group consisting of an energy-integrating detector element and a photon-counting detector element;
    with said energy-resolving monitor detector, detecting current dose measurement data of a portion of said x-ray radiation that does not proceed through the examination subject; and
    respectively emitting said two-dimensional radiation detector data and said energy-resolved current dose measurement data from said radiation detector and said monitor detector as respective electronic signals.

13. A method as claimed in claim 12, comprising, from a control unit, operating said x-ray source and said radiation detector as a computed tomography system to acquire said two-dimensional radiation detector data from said radiation detector as respective sets of projection data obtained by irradiating the examination subject from different directions.

14. A method as claimed in claim 12, comprising operating said x-ray source with respectively different x-ray energies in different time segments, and detecting energy data of said x-ray radiation in said different time segments from said energy-resolved dose measurement data acquired with said monitor detector.

15. A method to generate image data of an examination subject, comprising:
    providing a processor with two-dimensional radiation detector data from a radiation detector, said two-dimensional radiation detector data representing x-ray radiation attenuated by an examination subject;
    providing an energy-resolving monitor detector comprising at least two detector elements located in succession in a direction of propagation of said x-ray radiation, each of said at least two detector elements being a detector element selected from the group consisting of an energy-integrating detector element and a photon-counting detector element;

providing said processor with energy-resolved current dose measurement data acquired by said energy-resolving monitor detector from a portion of said x-ray radiation that does not proceed through the examination subject; and in said processor, executing an image reconstruction algorithm to generate image data of the examination subject from said two-dimensional radiation detector data and said energy-resolved current dose measurement data.

16. A method as claimed in claim 15, comprising providing said processor with sets of projection data, as said two-dimensional radiation detector data, respectively acquired by irradiating the examination subject from different directions.

17. A method as claimed in claim 15, comprising using said energy-resolved current dose measurement data in said image reconstruction algorithm to modify said two-dimensional detector data.

18. A method as claimed in claim 15, comprising, in said image reconstruction algorithm, using said energy-resolved dose measurement data to generate energy data representing an energy of the x-ray radiation, and using said energy data to generate mixed image data from said two-dimensional radiation detector data, said two-dimensional radiation detector data being acquired at different x-ray energies.

* * * * *